United States Patent [19]

Mawhinney et al.

[11] Patent Number: 4,467,037

[45] Date of Patent: Aug. 21, 1984

[54] SILYLATION OF AMINO ACIDS

[75] Inventors: Thomas P. Mawhinney, Columbia, Mo.; Michael A. Madson, Clear Lake, Iowa

[73] Assignee: The Curators of the University of Missouri, Columbia, Mo.

[21] Appl. No.: 353,358

[22] Filed: Mar. 1, 1982

[51] Int. Cl.$^3$ ............................................. G01N 31/08
[52] U.S. Cl. .................................... 436/89; 436/161; 436/174
[58] Field of Search ..................... 436/89, 90, 161, 174

[56] References Cited

PUBLICATIONS

Barzan et al., Journal of Chromatography, 236(1982), 201–207.
Donike et al., Journal of Chromatography, 202(1980), 483–486.
Kelly et al., Analytical Chemistry, vol. 48, No. 3, Mar. 1976.
Knapp "Handbook of Analytical Derivatization Reactions," John Wiley & Sons, 1979, pp. 8–10, 242–246, 270–277.

Primary Examiner—Arnold Turk
Attorney, Agent, or Firm—Grace J. Fishel

[57] ABSTRACT

An improved method for analyzing amino acids by silylation with silylating agents of the formulae:

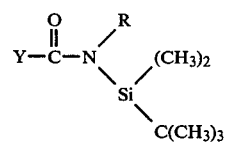

and

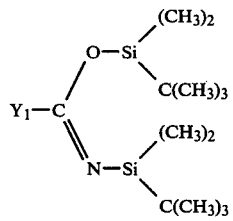

wherein R is lower alkyl, Y is hydrogen, lower alkyl or perfluoroloweralkyl and $Y_1$ is hydrogen or lower alkyl.

6 Claims, 1 Drawing Figure

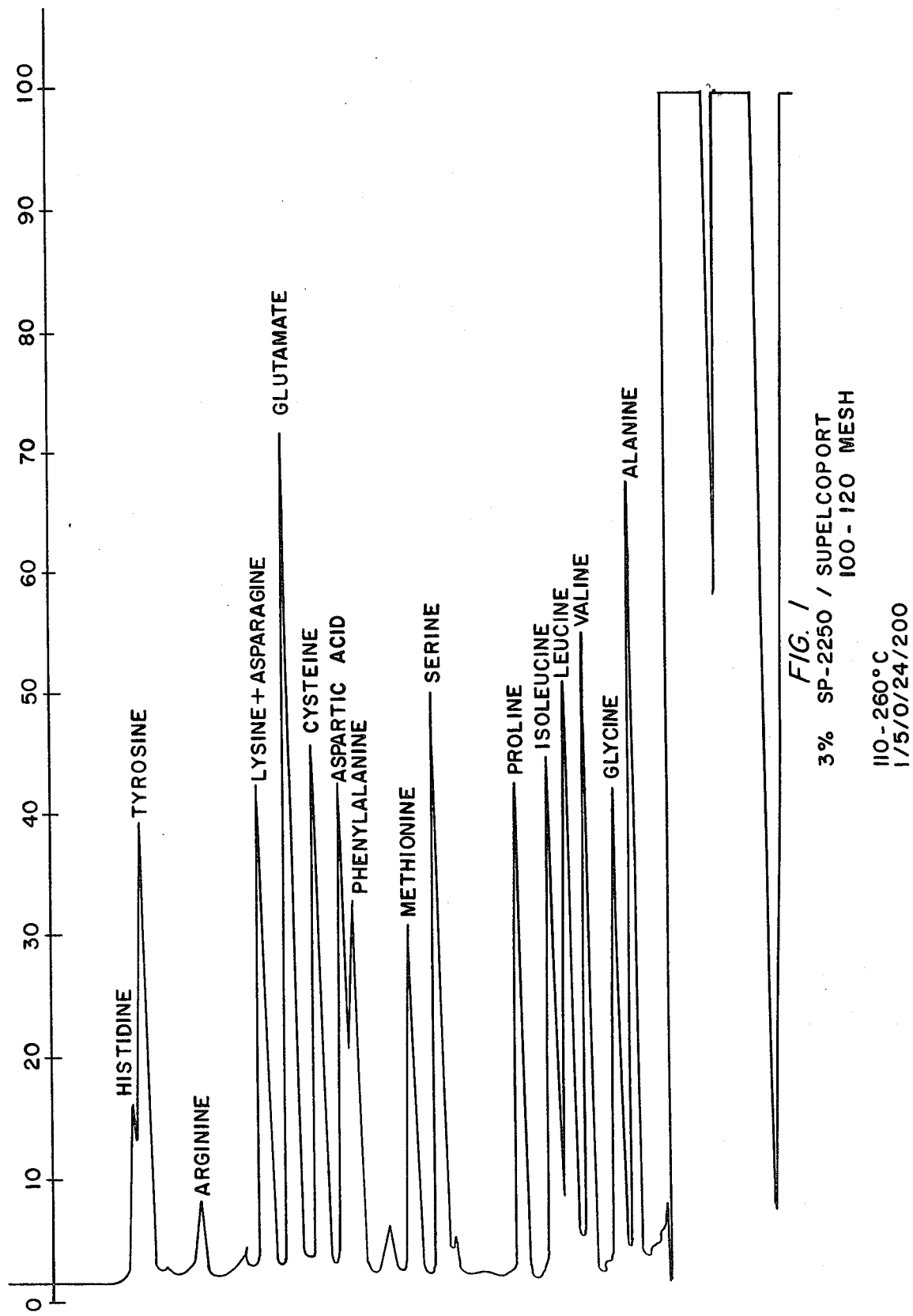

SILYATION OF AMINO ACIDS

The present invention relates to the analysis of amino acids by silylation. It particularly relates to the silylation of amino acids for analysis by gas chromatography.

BACKGROUND OF THE INVENTION

The replacement of an active hydrogen by a trialkylsilyl group reduces the polarity of a compound and decreases the possibility for hydrogen bonding. Consequently, where there is marked intermolecular hydrogen bonding in the parent compound the silylated derivative is usually more volatile. Further stability is enhanced upon silylation by reduction in the number of reactive sites with active hydrogen.

The advantages of volatility and stability imparted by silylation make the process a natural tool for gas-phase purification and analysis. In many cases the silylating agent and the compound are mixed at room temperature and the reaction is complete in a few minutes. The products generally can be distilled. They may be analyzed, without isolation, by gas chromatography, mass spectrometry or a combination of these techniques.

The greatest use of silylation has been for gas chromatography. Many hydroxy and amino compounds ordinarily regarded as nonvolatile or unstable at 200-300 degrees C have been successfully chromatographed after silylation.

Of particular utility among the many trialkyl silylating agents are those having a t-butyldimethylsilyl group. The most common of these agents is t-butyldimethylsilyl chloride which in the presence of a base such as imidazole or pyridine in a solvent such as N,N-dimethylformamide has been successfully used in the analysis of compounds containing a hydroxy group. Silylating agents having a t-butyldimethylsilyl group are preferred over their trimethylsilyl counterparts because of the ease with which the t-butyldimethylsilyl group can be removed under relative mild acidic or neutral conditions, and the relative high stability of the t-butyldimethylsilyl ethers to alkaline conditions, to hydrogenolysis and to reagents frequently used in organic synthesis, e.g., the Jones, Wittig and Grignard reagents. In addition, a t-butyldimethylsilyl ether is approximately 10,000 times more stable to solvolysis than the corresponding trimethylsilyl ethers.

While t-butyldimethylsilyl chloride has good utility with hydroxy containing compounds, no commonly used silylating agent, insofar as known, will yield volatile derivatives with amino acids such as the 18 common amino acids resulting from protein hydrolysis in acid sufficiently stable for analysis by gas chromatography. In addition, trimethylsilylating agents used to assay for some of these amino acids require prolonged heating periods.

In view of the above, it is an object of the present invention to provide an improved method for analyzing amino acids. Other objects and features will be in part apparent and in part pointed out hereinafter. The invention accordingly comprises the methods hereinafter described, the scope of the invention being indicated in the subjoined claims.

THE PRESENT INVENTION

The present invention provides an improved method for analyzing amino acids with t-butyldimethylsilyl donors which do not have the disadvantages of the presently used silylating agents. The method is rapid and accurate to the nanogram scale. FIG. 1 shows a typical run for amino acids in accordance with the present invention as t-butyldimethylsilyl derivatives by gas chromatography on a 3% SP-2250 column programmed from 110° C. to 260° C. at 5 degrees/minute.

In accordance with the present invention amino acids are reacted with a silylating agent of the formulae:

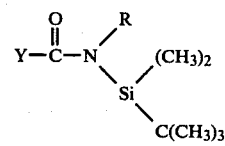

and

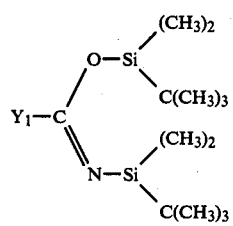

wherein R is lower alkyl having from 1 to 5 carbon atoms, Y is hydrogen, lower alkyl containing 1 to 5 carbon atoms or perfluoroloweralkyl having 1 to 5 carbon atoms, and $Y_1$ is hydrogen or lower alkyl having from 1 to 5 carbon atoms. The lower alkyl groups may be branched or straight-chained and include methyl, ethyl, propyl, isopropyl, butyl, sec-butyl, amyl, isoamyl and the like. Preferably, R is methyl and Y is hydrogen, methyl or trifluoromethyl and $Y_1$ is methyl.

Most of these compounds are clear liquids, easily transferable with a gas-tight syringe, and are readily soluble in most organic solvents.

The compounds are prepared by the reaction of t-butyldimethylsilyl chloride with an amide of the structure:

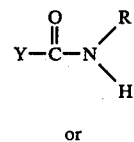

or

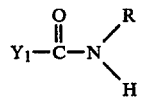

in the presence of a base which will not react with t-butyldimethylsilyl chloride. Suitable bases include sodium hydride, potassium hydride, lithium hydride, and tertiary amines such as pyridine, trimethylamine, triethylamine, N-methylmorpholine and the like and the product compounds may be isolated or, in some cases, formed in situ before they are used as silylating agents.

The above-described t-butyldimethylsilyl donars are used to analyze amino acids by silylating the amino acids under silylating conditions. Since the t-butyldimethylsilyl donars and their derivatives are more stable to moisture than their trimethylsilyl counterparts, the silylation can be conducted in the presence of a small amount of water. An excess amount of t-butyldimethysilyl donar is added to the sample above that necessary to react with the active hydrogens in the sample so that even though the sample is slightly wet, silylation of the sample is driven to completion.

Since the t-butyldimethylsilyl donars are flammable, the silylation is carried out under a nitrogen blanket. When the t-butyldimethylsilyl donar is a liquid, e.g. when the donar is N-methyl-N-t-butyldimethylsilyltrifluoroacetamide, N-methyl-N-t-butyldimethylsilylacetamide or N,O-bis-t-butyldimethylsilylacetamide, the silylation can be conducted in pure silylating agent without a solvent. In other cases, it is preferred that the reaction be carried out in a solvent such as acetonitrile or N,N-dimethylformamide.

Silylation of the amino acids occurs very quickly and in most cases is complete within 1 minute. A sample of the reaction mixture can then be injected directly into a gas chromatograph without further treatment. The solvent (if any) and the excess t-butyldimethylsilyl donar come off the column first, preconditioning it and removing any polar functions. The eluant from the chromatograph can then be analyzed in a mass spectrometer.

The invention will become clearer from the following examples which illustrate the invention.

EXAMPLE 1

N-methyl-N-t-butyldimethylsilyltrifluoroacetamide

To 800 ml of dry benzene:acetonitrile (v/v, 1:1) was added 127 g (1.0 mole) of N-methyl-trifluoroacetamide. To this solution, while stirring and maintaining the temperature at 0 degress C., was slowly added 23.5 g (0.98 mole) of sodium hydride. The solution was then stirred for 4 hours at 4 degrees C. At this time, 173.34 g (1.15 mole) of t-butyldimethylsilyl chloride was added in four equal aliquots over a period of 80 minutes. After the last addition the solution was stirred for 2 hours at 4 degrees C. The precipitate of sodium chloride was then removed from the reaction mixture by filtration under dry nitrogen and the resulting filter cake washed twice with 100 ml each of dry benzene. Washings and filtrate were combined and concentrated. The remaining yellow solution was fractionally distilled with the distillate at 158–172 degrees C. being collected. Redistillation of this fraction gave the desired product.

Yield, 91.3%; b. p. 168–170 degrees C. (760 mm); $d_4^{20}$ 1.121. $^1H$ NMR (CDCL$_3$) $\delta$0.28 (tetramethylsilane having $\delta$0.00), (s,6H, Si(CH$_3$)$_2$), 0.98 (s,9H,SiC(CH$_3$)$_3$), 3.08 (s,3H,N(CH$_3$); mass spectrum, m/e (relative intensity) 241 (M$^{30}$, 18), 226 (22), 184 (100), 147 (79), 145 (52), 130 (18), 127 (33), 113 (20).

Analysis calculated for C$_9$H$_{18}$F$_3$NOSi: C, 44.79; H, 7.52; N, 5.80; Si, 11.64.

Found: C, 44.47; H, 7.46; N, 5.69; Si, 11.50.

EXAMPLE 2

N-methyl-N-t-butyldimethylsilylacetamide

To a vigorously stirred solution of 73.1 g (1.0 mole) N-methylacetamide dissolved in 1400 ml of dry triethylamine was added 196 g (1.30 mole) of t-butyldimethylsilyl chloride. The flask was purged with dry nitrogen and then equipped with a drying tube. Hard stirring of the mixture was continued for 24 hours at room temperature. Then, under a layer of dry air, the reaction mixture was filtered to remove the precipitate of triethylamine hydrochloride. The resulting filter cake was then washed three times with 150 ml each of dry triethylamine. The filtrate and washings were combined and reduced in volume by distillation at 35 degrees C. at 10 mm Hg. The remaining straw colored liquid was then fractionally distilled.

Yield, 88%, b. p. 57–59 degrees C. (1.0 mm); $d_4^{20}$ 0.8997. H$^1$ NMR (CDCL$_3$) $\delta$0.26 (s, 6H, N-Si(CH$_3$)$_2$), 0.94 (s,9H,N-Si(CH$_3$)$_3$), 2.05 (s,3H,CH$_3$—C), 2.79 (s,3H,N(CH$_3$)); mass spectrum, m/e (relative intensity) 187 (M+, 11), 127 (17), 130 (100), 147 (74), 73 (66), 59 (93).

Analysis calculated for C$_9$H$_{21}$NOSi: C, 57.70; H, 11.30; N, 7.48; Si, 14.99. Found: C, 57.32; H, 11.12; N, 7.59; Si, 14.96.

EXAMPLE 3

N-methyl-N-t-butyldimethylsilylformamide

The procedure of Example 2 was followed except that 59.01 g (1.0 mole) of N-methylformamide was used in place of N-methylacetamide.

Yield, 93%, b. p. 84–85 degrees C. (1.2 mm); m. p. 32 degrees C. (moist solid). $^1H$ NMR (CDCL$_3$) $\delta$0.29 (s,6H,N-Si(CH$_3$)$_2$), 0.93 (s,9H,SiC(CH$_3$)$_3$), 2.76 (s,3H,N(CH$_3$)), 8.27 (s,1H,H—C); mass spectrum, m/e (relative intensity) 173 (M$^{30}$, 18), 158 (22), 147 (67), 116 (100), 59 (86).

Analysis calculated for C$_8$H$_{19}$NOSi: C, 55.44; H, 11.05; N, 8.08; Si, 16.20. Found: C, 55.63; H, 10.88; N, 8.19; Si, 15.99.

EXAMPLE 4

N,O-bis-t-butyldimethylsilylacetamide

The procedure of Example 2 was followed except that 29.5 g (0.5 mole) of acetamide was used in place of N-methylacetamide.

Yield, 88.7% b.p. 91–92 degrees C. (2.0 mm); $d_4^{20}$ 0.859. $^1H$ NMR (CDCL$_3$) $\delta$0.06 (s,6H,O-Si(CH$_3$)$_2$), 0.22 (s,6H,N-Si(CH$_3$)$_2$), 0.87 (s,18H,(Si-C(CH$_3$)$_3$)$_2$), 1.93 (s,3H,CH$_3$—C); mass spectrum, m/e (relative intensity) 287 (M+, 15), 272 (13), 230 (100), 189 (33), 155 (78), 147 (74), 116 (22).

Analysis calculated for C$_{14}$H$_{33}$NOSi$_2$: C, 58.47; H, 11.57; N, 4.87; Si, 19.53. Found: C, 58.28; H, 11.52; N, 11.61; Si, 19.44.

EXAMPLE 5

In accordance with the present invention, the t-butyldimethylsilyl donars prepared in the foregoing examples were used to silylate amino acids in a clinical sample of proteins which had been acid hydrolyzed into their component amino acids. The silylations were performed under dry nitrogen in TEFLON faced septum capped reaction vials and flasks. Prior to silylation, the amino acid sample was dissolved in a minimal amount of either dry acetonitrile or N,N-dimethylformamide. Silylation was accomplished by adding 10.0 equivalents based on the number of silylatable functions of a t-butyldimethylsilyl donor of the above formulae. While the t-butyldimethylsilylating agent may be used alone, it is preferred to add a non-interfering acid as a catalyst such as 1% by weight of t-butyldimethylsilyl chloride.

The t-butyldimethylsilyl donor reacts readily with all 18 common amino acids at room temperature and within about 1 minute producing derivatives that when chromatographed yield very symmetrical, sharp peaks for each amino acid as shown in FIG. 1 when the reaction mixture is chromatographed on a column. Separation of the amino acids is ideal and samples of the eluant from the gas chromatograph were then analyzed in a mass spectrometer.

In view of the above, it will be seen that several objects of the invention are achieved and other advantageous results attained. As various changes could be made in the above methods without departing from the scope of the invention, it is intended that all matter contained in the above description or shown in the accompanying drawing shall be interpreted as illustrative and not in a limiting sense.

What is claimed is:

1. In a method for analyzing amino acids by silylating said amino acids under silylating conditions with a silylating agent, the improvement which comprises selecting the silylating agent from compounds having the structure:

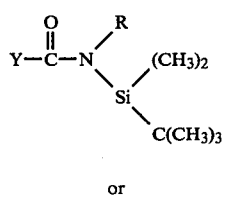

or

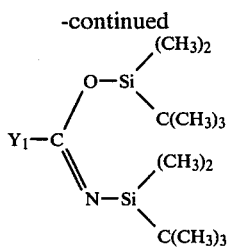

wherein:
R is lower alkyl having 1 to 5 carbon atoms,
Y is hydrogen, lower alkyl having 1 to 5 carbon atoms, or perfluoroloweralkyl having 1 to 5 carbon atoms, and
$Y_1$ is hydrogen or lower alkyl having 1 to 5 carbon atoms.

2. The method according to claim 1 wherein R is methyl.

3. The method according to claim 2 wherein Y is hydrogen.

4. The method according to claim 2 wherein Y is methyl.

5. The method according to claim 2 wherein Y is trifluoromethyl.

6. The method according to claim 1 wherein $Y_1$ is methyl.

* * * * *